United States Patent
Mitchell et al.

(10) Patent No.: US 7,070,738 B2
(45) Date of Patent: Jul. 4, 2006

(54) ANALYZER WITH VARIABLE VOLUME BALLAST CHAMBER AND METHOD OF ANALYSIS

(75) Inventors: Joel C. Mitchell, Bridgman, MI (US); John T. Hoss, Stevensville, MI (US); Mark A. Hartfield, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 0 days.

(21) Appl. No.: 10/780,940

(22) Filed: Feb. 18, 2004

(65) Prior Publication Data

US 2004/0171165 A1  Sep. 2, 2004

Related U.S. Application Data

(60) Provisional application No. 60/450,635, filed on Feb. 28, 2003.

(51) Int. Cl.
*B32B 5/02* (2006.01)

(52) U.S. Cl. ........................................ 422/78
(58) Field of Classification Search .................. 422/78
See application file for complete search history.

(56) References Cited

U.S. PATENT DOCUMENTS

| | | | |
|---|---|---|---|
| 3,698,869 A * | 10/1972 | Condon | 436/115 |
| 4,525,328 A | 6/1985 | Bredeweg | |
| 4,527,436 A * | 7/1985 | Jones | 73/863.84 |
| 4,573,910 A | 3/1986 | Bredeweg | |
| 4,622,009 A * | 11/1986 | Bredeweg | 432/156 |
| 4,627,267 A * | 12/1986 | Cohrs et al. | 73/1.22 |
| 5,563,339 A * | 10/1996 | Compton et al. | 73/64.45 |
| 6,207,460 B1 | 3/2001 | Kishkovich et al. | |
| 6,270,727 B1 | 8/2001 | Mitchell et al. | |
| 6,291,802 B1 | 9/2001 | Ford | |
| 6,623,699 B1 | 9/2003 | Pack et al. | |

OTHER PUBLICATIONS

*Instrumental Organic Elemental Analysis*, 1977, "1. The Perkin-Elmer Model 240 Elemental Analyzer: Carbon, Hydrogen and Nitrogen" M. R. Cottrell and f. H. Cottrell.

* cited by examiner

*Primary Examiner*—Jill Warden
*Assistant Examiner*—Natalia Levkovich
(74) *Attorney, Agent, or Firm*—Price, Heneveld, Cooper, DeWitt & Litton, LLP

(57) ABSTRACT

An analyzer having a combustion furnace includes a gas flow stream including a combustion detector in the stream of byproducts of combustion and a variable volume ballast chamber for receiving byproducts of combustion and which has a movable piston which moves in response to the introduced combustion byproducts. Subsequently, an aliquot sample from the chamber is forced through detectors for elements being detected. The method of analysis incorporating the present invention includes filling a variable volume ballast chamber with byproducts of combustion until combustion completion has been detected and, subsequently, forcing at least an aliquot sample of the combustion byproducts from the variable volume ballast chamber into a flow path including detectors for the elements of interest.

34 Claims, 3 Drawing Sheets

ANALYZER WITH VARIABLE VOLUME BALLAST CHAMBER AND METHOD OF ANALYSIS

CROSS-REFERENCE TO RELATED APPLICATIONS

This application claims priority under 35 U.S.C. § 119(e) on U.S. Provisional Application No. 60/450,635 entitled ELEMENTAL ANALYZER, filed on Feb. 28, 2003, by Joel C. Mitchell, et al., the entire disclosure of which is incorporated herein by reference.

BACKGROUND OF THE INVENTION

The present invention relates to elemental analyzers and analytical methods, particularly an analyzer employing a variable volume ballast chamber and its use for the collection of analytes and their subsequent analysis.

The determination of elements, such as carbon, hydrogen, and nitrogen, in an organic material is desirable for numerous reasons. Elemental analyzers, such as a CHN 2000 which is commercially available from Leco Corporation of St. Joseph, Michigan, have been used for a variety of applications. In recent years, the food market has become interested in determining the amount of protein in a sample which can be determined by the nitrogen content. Thus, the determination of nitrogen is important in providing such useful information to the nutritional market. The carbon-to-hydrogen ratio is desirable in the characterization of coal and coke samples, as is the carbon, hydrogen, and nitrogen ratios in a variety of other organic materials. Thus, elemental analyzers have been in use for these and other applications for some time.

Generally, the analysis of elemental carbon hydrogen and nitrogen is well known and is discussed in several references, including *Methods in Microanalysis*, Vol. 1, Mirra Osipovna Korshun, 1964, *Instrumental Organic Elemental Analysis*, R. Belcher, 1977; and *Organic Elemental Analysis Ultramicro, Micro, and Trace Methods*, Wolfgang J. Kirsten, 1983. U.S. Pat. No. 4,525,328 discloses an analyzer employing a fixed volume ballast chamber, which collects analytes in an approximately 4.5 L chamber for subsequent analysis. Such a system eliminates the rapid fouling of the various reducing agents and absorbing agents used in the system by the collection of a sample in the chamber and subsequent detection of an aliquot of the collected sample. The amount of combustion oxygen used in filling the fixed ballast chamber is significant, and an analysis takes a significant amount of time for the combustion and ballast chamber filling. Also, the byproducts of combustion, i.e., the analyte gases, are somewhat diluted in the relatively large volume ballast chamber. Thus, there remains a need to provide an elemental analyzer which uses less oxygen, is faster, and is more sensitive, particularly when relatively small samples are being analyzed.

SUMMARY OF THE INVENTION

The present invention improves upon the fixed ballast system of the prior art by providing a variable volume ballast chamber with a movable piston and a combustion detector, such that, during combustion of a sample, the chamber is only filled with byproducts of combustion until completion of combustion as determined by a combustion detector. Typically, a significantly smaller volume than that of the fixed volume ballast chamber is captured in a more concentrated form of analyte which subsequently can be ejected from the variable volume ballast chamber by controlling a movable piston. An aliquot sample is extracted from the ballast chamber and passes through carbon and hydrogen detectors and into a doser valve for subsequent detection of nitrogen. By employing a variable volume ballast chamber and detecting the combustion completion, the concentration of the byproducts of combustion is higher, and this higher concentration allows more accurate results, which can be obtained more quickly. In a preferred embodiment, the position of the variable volume ballast chamber is detected, as is the chamber pressure, to provide variable ballast fill dilution and pressure dilution correction factors for the analyzer.

The system of the present invention includes an analyzer having a combustion furnace, a gas flow stream including a combustion detector in the stream of byproducts of combustion from the combustion furnace and a variable volume ballast chamber comprising a chamber having a movable piston which moves in response to the introduced combustion byproducts to a position within the chamber until such time as completion of combustion is detected. Subsequently, the inlet of the ballast chamber is sealed, and the outlet is opened. The piston is then moved to force an aliquot sample through detectors for elements being detected.

The method of analysis incorporating the present invention includes filling a variable volume ballast chamber with byproducts of combustion until combustion completion has been detected and, subsequently, forcing at least a sample of the combustion byproducts from the variable volume ballast chamber into a flow path including detectors for the elements of interest.

As a result of the utilization of such a system and method, a faster analysis can be obtained since a smaller volume of byproducts of combustion are collected, the system employs less oxygen for the combustion of the sample and transportation of the byproducts of combustion into the variable volume ballast chamber, and the byproducts collected are more concentrated for more accurate analysis. These and other features, objects and advantages of the present invention will become apparent upon reading the following description thereof together with reference to the accompanying drawings.

DETAILED DESCRIPTION OF THE PREFERRED EMBODIMENT

The analytical method of the present invention involves two phases. The first phase is the combustion and collection phase utilizing oxygen as the combustion and carrier gas which is supplied to a combustion furnace with the byproducts of combustion being filtered and transported through a combustion detector and collected in a variable volume ballast chamber. The combustion phase is then followed by an analysis phase in which the collected byproducts of combustion are ejected from the variable volume ballast chamber into detectors in flow paths, including one for the detection of carbon and hydrogen utilizing infrared detectors and a second one for nitrogen utilizing thermal conductivity cells.

Figure 1:
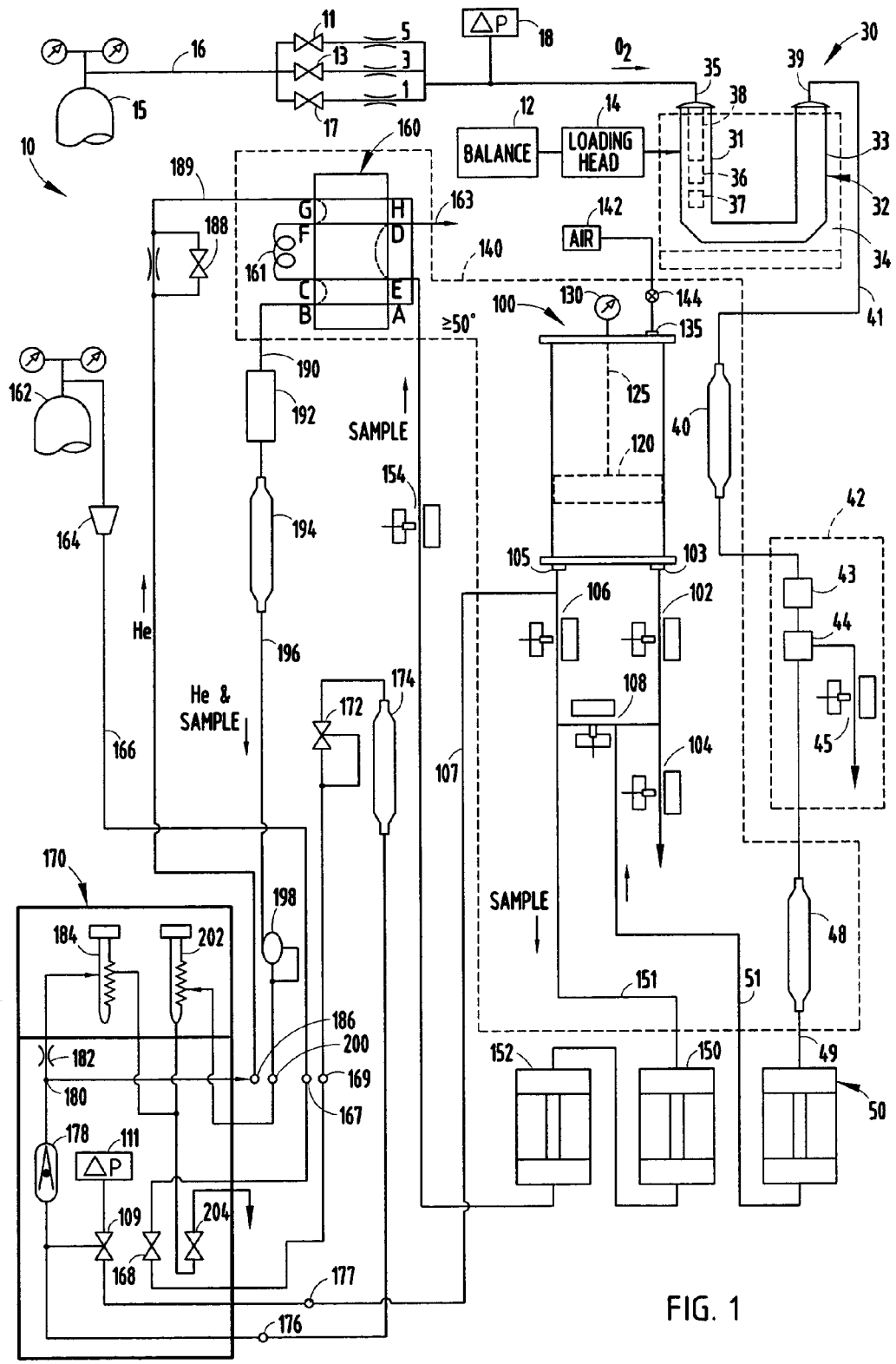
FIG. 1 is a flow diagram, partly in block and schematic form, of an analyzer embodying the variable volume ballast chamber of the present invention.

The overall system is best seen in FIG. 1, in which an analyzer 10 embodying the present invention is shown. The analyzer includes a resistance combustion furnace 30 which includes a generally U-shaped combustion tube 32 having a combustion leg 31 and an afterburner leg 33. Combustion furnace 30 is generally of the type disclosed in U.S. Pat. No. 4,525,328 and heats a sample weighed by balance 12 and introduced by a zero blank loading head 14 into the combustion furnace 30, particularly, the inlet 35 of combustion leg 31 thereof. The loading head may be of the type disclosed in U.S. Pat. No. 6,291,802, which introduces samples by gravity drop into the open mouth of a ceramic combustion crucible 36 of the type disclosed in U.S. Pat. No. 6,270,727. Crucible 36 is held within the combustion tube leg 31 by a porous support plug 37 allowing gas to pass therethrough. The afterburner leg 33 of combustion tube 32 includes reagents, such as alumina and calcium oxide, held therein by quartz wool plugs to facilitate combustion and remove undesirable combustion byproducts, such as the oxides of sulfur. Other reagents can be employed if other material is desired to be removed, as is well known by those skilled in the art.

Combustion furnace 30 is heated by a resistance heater 34 surrounding the legs 31 and 33 of the generally U-shaped tube 32 to a temperature of approximately 1000° C. Samples to be combusted typically are 1 gram samples and are either standards for the calibration and testing of the instrument or actual samples of any organic material which may include food products, coal, coke, or other organic substances. The analyzer 10 of the present invention, however, can be used with smaller samples due to the use of the unique variable volume ballast chamber 100 as described below.

Inlet 35 of furnace 30 also receives combustion gas ($O_2$) from a source 15 of oxygen which has a flow rate adjusted between 0.5, 1, 3, 5, or 6 L per minute by the selective activation of parallel flow control valves 11, 13, and 17 in conduit 16 leading from the supply of oxygen to the inlet 35 of the combustion furnace. The $O_2$ pressure is monitored by pressure sensor 18. The oxygen is jetted into the open mouth of a sample-holding crucible 36 through an oxygen lance 38 to combust the sample. The byproducts of combustion (i.e., analytes) flow through reagents in leg 33 and from combustion chamber 30 at exit port 39. Conduit 41 transfers the byproducts of combustion through a first scrubber 40, which can be steel wool or an anhydrone material to filter particulates from the gas stream.

Depending on whether or not hydrogen is being sampled, water is removed from the system utilizing a cooler 42 including a precooler 43 and a thermoelectric cooler 44 having a drain valve 45, which is normally closed during combustion, and opened only when the collected water and impurities carried therein are drained. If, however, hydrogen is desired to be detected, the scrubber 40 is coupled directly to a secondary scrubber 48 bypassing cooler 42. Scrubber 48 is a second particulate filter with finer filtering media to filter particulate matter from about 10 to 100 microns from the gas flow stream. The filtered byproducts of combustion flowing in conduit 49 then pass through a combustion detector 50 comprising a $CO_2$ IR cell, which monitors the $CO_2$ in the gas stream as a result of the combustion of the sample in crucible 36.

Figure 3:
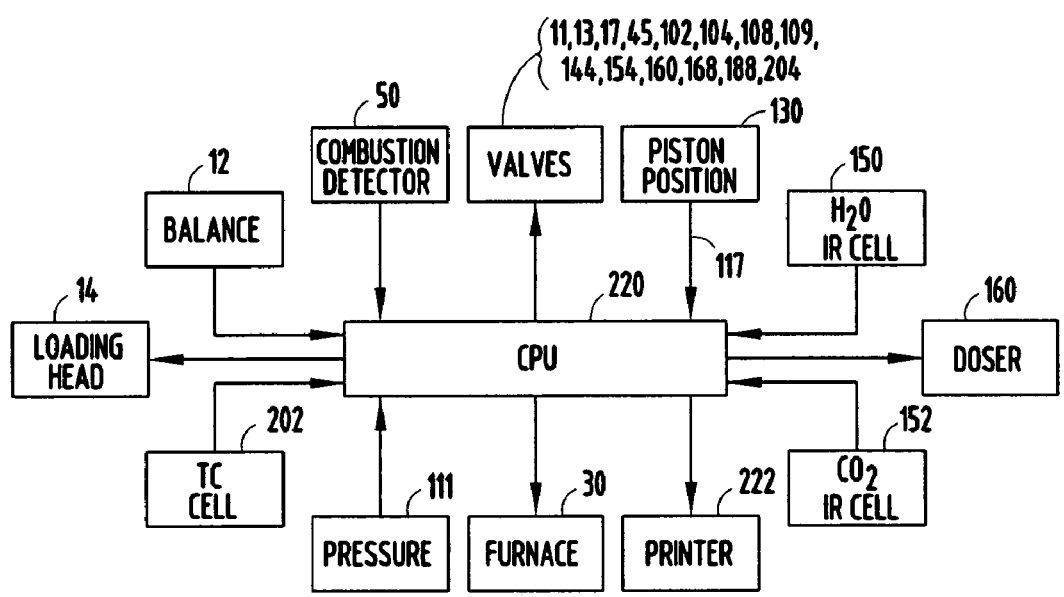
FIG. 3 is an electrical circuit diagram in block form of the control system for the analyzer of the present invention.

The combustion detector 50 is coupled to the CPU 220 shown in FIG. 3, which monitors when the peak of $CO_2$ concentration has occurred and the peak has decayed about 90% to about 99.9%, and preferably about 99% to allow all the combusted gases to be collected by the variable volume ballast chamber 100. If the analysis includes hydrogen, then the $CO_2$ combustion monitor detector is replaced with a $H_2O$ detector for monitoring the combustion process. During combustion, the inlet valve 102 of variable volume ballast chamber 100 is opened to allow the analytes in conduit 51 to enter chamber 100. During this time, the exhaust valve 104, the discharge valve 106, and the purge valve 108 are closed. The $O_2$ carrier gas and byproducts of combustion accordingly flow into chamber 100. Upon detection of completion of combustion, CPU 220 controls the various valves as described below to complete the analyte collection phase and subsequently enter the gas analysis phase of operation of analyzer 10.

Figure 2:
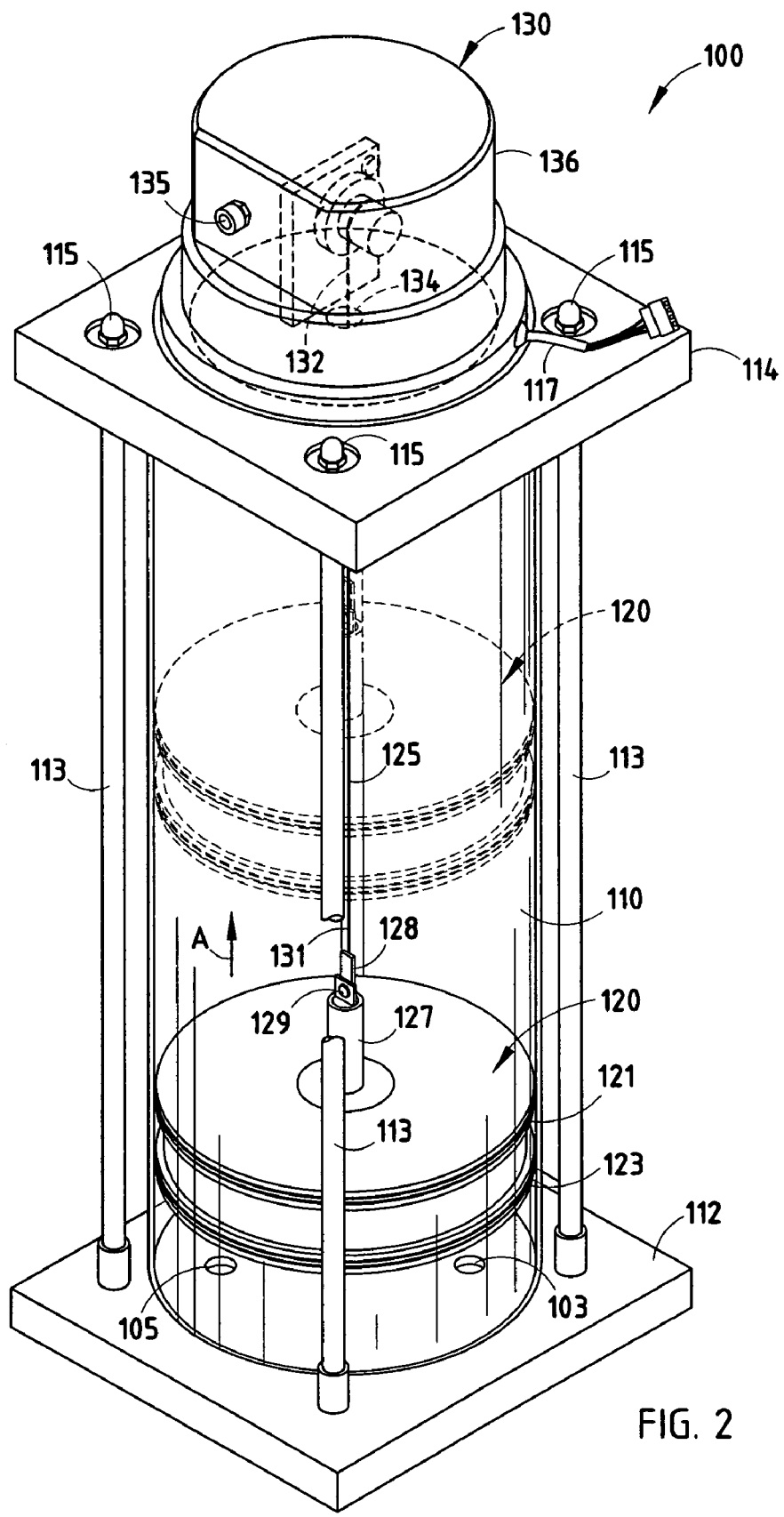
FIG. 2 is a perspective view of the variable volume ballast chamber of the present invention.

The variable volume ballast 100 is shown in FIG. 2 and includes a generally cylindrical container 110 sealably coupled to a base 112 and to a sealed cover 114 and a sealed cap 136. The container is secured between cover 114 and base 112 utilizing threaded rods 113 and cap nuts 115. The cylindrical container 110 preferably is made of a precision bore clear material, such as Pyrex®, and houses a movable piston 120 which includes a pair of vertically spaced O-rings 121 and 123 providing a seal between the inner wall of cylindrical container 110 and piston 120. The inlet valve 102, shown in FIG. 1, is coupled to an inlet port 103 extending through the base 112 of chamber 100. The pressurized byproducts of combustion (at about 1.7 PSI) during combustion urge piston 120 upwardly in the direction indicated by arrow A in FIG. 2, until such time as the completion of combustion is detected by detector 50 and the CPU 220 (shown in FIG. 3) closes the inlet valve 102 and the oxygen flow valves 11, 13, an 17. Piston 120 is coupled to a rotary encoder 130 by means of a cable 125 coupled to the top of the piston and extending through aperture 134 in cover 114. Cable 125 is coupled to the piston 120 by means of a suitable fitting 127, including a spade lug 128 on the end of cable 125 and a fastener-receiving post 129 on fitting 127. The rotary encoder 130 coupled to cable 125 can be a model PTX150, commercially available from Celesco Transducer Products of Chatsworth, Calif. or an equivalent. The lower end 131 of cable 125 is coupled to the piston and the upper end 132 is coupled to the rotary encoder 130, which is electrically coupled by a suitable connecting cable 117 to the CPU 220 of FIG. 3. Encoder 130 provides data indicative of the position of piston 120 after combustion which, as described below, is employed to provide a fill volume dilution correction factor.

In view of the known diameter of the cylindrical container 110 and the detected height of the lower surface 124 of the piston 120 from base 112, the volume of gas contained in the variable volume ballast chamber 100, after combustion, can be determined. The control valves 102 through 108, the variable volume ballast chamber 100, and the doser valve 160 are held to a constant temperature of approximately 50° C., as shown by the dotted line heated chamber 140 in FIG. 1, such that the relationship between the gas volume and concentration as set forth in the universal gas law $PV=nRT$, removes the temperature as a variable in this equation. The concentration of gas, i.e., the number of moles of gas (n), is a direct function of the volume of the collected gas and its pressure. The volume, on the other hand, is directly related to the displacement of piston 120, such that the concentration of collected analytes in the chamber 110 below piston 120 can be determined directly as a function of the displacement of the piston. Thus, if piston 120 moves one-quarter of the distance from the surface of base 112, as opposed to half of the distance, the concentration of collected gases is twice that as compared to a collection which results in the piston moving half way to the end of the chamber. This detection of the position of the piston is employed by the CPU 220 in providing a volume dilution correction factor (VCF) correcting for the concentration of gas as compared to a standard set of conditions (STP) according to the formula:

$$V_{CF} = \frac{Vd}{Vs}$$

where Vd is the detected volume after combustion based upon the movement of the piston; and Vs is the volume under a standardized known condition.

The concentration of gas is also a direct function of pressure within ballast chamber 100 which is also measured by a pressure sensor 111 (FIG. 1) coupled to output port 105 (FIG. 2) of chamber 100 via conduit 107 coupled to port 177 of thermal conductivity module 170 and to a three-way valve 109. Valve 109 is also used to monitor the helium carrier gas pressure when in the other position. This pressure measurement, taken upon completion of combustion, is employed to provide a pressure dilution correction factor (PCF) against a standard pressure for the final calculation of measured analytes according to the formula:

$$P_{CF} = \frac{Pd}{Ps}$$

where Pd is the detected pressure after combustion; and

Ps is the pressure under a standard known condition.

These correction factors (VCF and PCF) are employed by the program of the CPU 220 to provide the final concentration of elements detected by the various detectors employed by the analyzer as now described.

Once the gas has been collected, after combustion detector 50 determines combustion has completed for the slowest moving analyte through the system, valve 102 is closed and the gases in chamber 100 are allowed to equilibrate for a period of approximately 20 seconds. The piston position is determined by encoder 130 and supplied to memory within CPU 220, which converts it to Vd. Similarly, the pressure Pd from sensor 111 is stored in CPU memory. After the gases are allowed to equilibrate, valve 106 is opened, and some of the byproducts of combustion collected in chamber 100 are forced outwardly by the application of air pressure through an air inlet fitting 135 in sealed cap 136 communicating with aperture 134 in the top wall 114 of chamber 100 (FIG. 2) from a 12 psi supply of pressurized fluid, such as air from supply 142 (FIG. 1), and through valve 144 controlled by CPU 220.

As seen in FIG. 1, the byproducts of combustion are forced through a flow path including conduit 151, an $H_2$ determining IR cell 150, and a C determining IR cell 152 and then through a now opened valve 154 into port E of doser valve 160, also contained within heated chamber 140. The sample gas then travels to port C through doser loop 161 to port F and through the exhaust tube 163 coupled to port D. The sample gas is pushed through this flow path by the movement of piston 120 for about 15 seconds. Simultaneously, He carrier gas from source 162 flows through filter 164 in conduit 166 to inlet port 167 of thermal conductivity module 170 via the actuation of He valve 168. The He gas exits module 170 via port 169, travels through a 12 psi pressure regulator 172 and scrubber 174 into port 176 of thermal conductivity module 170. This He then flows through a flow measuring device 178 to T junction 180. Some of the He then exits thermal conductivity module 170 through port 186 and valve 188. The He then flows into port G of doser valve 160. From there, the loop load is achieved by He exiting at port H bypassing to port A, and exiting the doser valve at port B.

After the 15 second loop loading interval, valves 106 and 154 are turned off by CPU 220, and the about 3 ml aliquot of sample gas in doser loop 161 is allowed to equilibrate for about 2 seconds. The $H_2O$ and $CO_2$ IR detectors are then read by the CPU, and the CPU activates doser valve 160. The He carrier gas now sweeps from port G to port F (as shown in dotted lines) in doser 160 through loop 161 and from port C to B, carrying the sample gas into conduit 190. The sample gas and He then flows into a reduction tube 192 filled with copper (Cu) heated to about 750° C. to remove any remaining oxygen and convert NO to free nitrogen ($N_2$), which subsequently flows through a scrubber 194 which includes sodium hydrate silicate for removing $CO_2$ and an anhydrone, which removes water from the gas flow stream.

The now free nitrogen and helium carrier in conduit 196 flows through a 300 cc per minute flow controller 198 and into the nitrogen sample inlet port 200 of thermal conductivity module 170 and through the thermal conductivity measurement device 202, which is coupled to CPU 220 to provide data relative to the nitrogen concentration detected. After measurement, the gas is then exhausted through an exhaust outlet valve 204. During the measurement of nitrogen concentration by cell 202, He carrier gas at T junction 180, also flows through a flow restrictor 182 to a thermal conductivity reference cell 184, while the second flow path of helium exits thermal conductivity module at port 186.

The analysis flow path allows gas from variable volume ballast chamber 100 to provide an aliquot of the gas collected, which has a relatively high concentration and which can be normalized against a standard by detecting the position of piston 120. The control of the valves and the combustion furnace, as well as the measurement and detection of the volume and, therefore, concentration of gas is controlled by CPU 220 shown in FIG. 3. The CPU receives an input signal as to the size of the sample from balance 12 and controls the loading head 14 to drop the sample within the combustion chamber. The CPU also controls the application of power to furnace 30 through a suitable power control module. The CPU is also programmed to control the operation of valves 11, 13, 17, 45, 102, 104, 106, 108, 109, 144, 154, 160, 168, 188, and 204, in the sequence discussed above. The combustion completion detector 50 provides input signals to the CPU which determines when the combustion has been completed and valve 102 closed, at which time the CPU receives data from the piston position sensor 130 for the variable volume ballast chamber 100. The $H_2O$ detector 150 provides input signals to the CPU relating to the concentration of hydrogen detected, while the $CO_2$ detector 152 provides signals to the CPU regarding the amount of carbon detected. Finally, the thermal conductivity detector 202 coupled to the CPU provides the CPU with a signal representing the nitrogen level detected in the sample. The CPU may be coupled to a printer 222 to print the results of the concentration detected. The CPU is programmed in a conventional manner, to analyze the sample based upon standard ASTM standards utilizing data from the infrared detectors and thermal conductivity detectors shown in FIG. 1.

The CPU is also programmed to apply the correction factors (V$_{CF}$ and P$_{CF}$) to the detected concentration of sample gases based upon the relative volume of gas collected by utilization of signals from the rotary encoder 130 and the pressure detected by sensor 111. These signals are linearly related to the volume of gas collected as well as the concentration of collected gas within container 110. This allows a relatively smaller and more concentrated amount of analyte gases to be collected more quickly and utilizing less oxygen by the completion of combustion and the measurement of the volume of gas collected in container 110. As is well known after an analysis cycle, the analyzer is purged to condition it for a subsequent analysis. The O$_2$ from source 15 is employed to purge the combustion loop and exhausts through opened valve 104 while He from source 162 purges the doser loop and exhausts through opened valve 204. By the use of a variable volume ballast chamber and a combustion detector, an improved analyzer is provided for the analysis of analytes of combustion and one which is more accurate, faster to use, and employs less oxygen during the analysis.

It will become apparent to those skilled in the art that various modifications to the preferred embodiment of the invention as described herein can be made without departing from the spirit or scope of the invention as defined by the appended claims.

The invention claimed is:

1. An analyzer comprising:
 a combustion furnace for receiving samples for combustion;
 a combustion detector coupled in a flow path of byproducts of combustion from said combustion furnace for determining when combustion is completed;
 a variable volume ballast chamber coupled to the flow path of combustion byproducts for receiving byproducts of combustion until combustion has been completed, said variable volume ballast chamber including a movable piston and a sensor for detecting the position of said piston; and
 a control coupled to said sensor for the detection of the position of the piston and calculating a volume correction factor for the concentration of gases of the byproducts of combustion based upon the position of said piston.

2. The analyzer as defined in claim 1 wherein said combustion detector detects CO$_2$.

3. The analyzer as defined in claim 1 wherein said combustion detector detects H$_2$O.

4. The analyzer as defined in claim 1 wherein said variable volume ballast chamber comprises a cylindrical container and said sensor is a rotary encoder coupled to said piston by a cable.

5. The analyzer as defined in claim 4 wherein said cylindrical container has a sample gas inlet and a sample gas outlet at one end and a first control valve associated with said inlet and a second control valve associated with said outlet to control the entry and exit of sample gas into said variable volume ballast chamber.

6. The analyzer as defined in claim 5 wherein said cylindrical container includes a fluid inlet at an end opposite said one end and on a side of said piston opposite said sample gas inlet and a fluid control valve coupled to a source of pressurized fluid to selectively move said piston to force sample gas from said variable volume ballast chamber through said sample gas outlet.

7. The analyzer as defined in claim 6 wherein each of said first, second and fluid control valves are coupled to said control for sequentially actuating said valves to introduce sample gas into said variable volume ballast chamber, allow said sample gas to equilibrate in said variable volume ballast chamber, and subsequently discharge sample gas from said variable volume ballast chamber.

8. The analyzer as defined in claim 7 wherein a H$_2$O sensor is coupled to said gas outlet of said variable volume ballast chamber to detect the concentration of H$_2$ during an analysis.

9. The analyzer as defined in claim 7 wherein a CO$_2$ sensor is coupled to said gas outlet of said variable volume ballast chamber to detect the concentration of C during an analysis.

10. A method of determining the concentration of elemental elements in a sample including the steps of:
 combusting a sample;
 collecting the byproduct gases of combustion in a variable volume ballast chamber;
 detecting the completion of combustion; and
 measuring the volume of gases collected by the variable volume ballast chamber upon completion of combustion.

11. The method as defined in claim 10 wherein said collecting step comprises introducing byproduct gases of combustion into a sample gas inlet in a container having a movable piston such that said piston moves in response to the introduction of byproduct gases of combustion until combustion has been completed as determined by said detecting step.

12. The method as defined in claim 11 wherein said collecting step further includes sequentially actuating an inlet valve associated with said sample gas inlet and an outlet valve associated with a sample gas outlet in said container to introduce and capture byproduct gases of combustion.

13. The method as defined in claim 12 wherein said collecting step further includes actuating a control valve coupled to a fluid inlet in said container on a side of said piston opposite said sample gas outlet for supplying pressurized fluid to said piston to force byproduct gases of combustion from said container.

14. The method as defined in claim 13 wherein said collecting step further includes allowing a period of time sufficient for said byproduct gases of combustion to equilibrate before forcing said byproduct gases of combustion from said container.

15. The method as defined in claim 14 wherein said detecting step comprises detecting CO$_2$ in a stream of said byproduct gases of combustion before introduction into said container.

16. The method as defined in claim 10 wherein said measuring step comprises sensing the position of said piston.

17. The method as defined in claim 16 wherein said sensing step comprises coupling said piston to an encoder through a cable such that as said piston moves said encoder provides information as to the piston position which corresponds directly to the volume of collected byproduct gases of combustion.

18. The method as defined in claim 10 and further providing a volume correction factor for the determination of the concentration of an element according to the formula:

$$V_{CF} = \frac{Vd}{Vs}$$

where Vd is the detected volume after combustion based upon the movement of the piston; and Vs is the volume under a standardized known condition.

19. The method as defined in claim 10 and further including detecting the pressure of collected byproducts of combustion in said variable volume ballast chamber.

20. The method as defined in claim 19 and further providing a pressure correction factor for the determination of the concentration of an element according to the formula:

$$P_{CF} = \frac{Pd}{Ps}$$

where Pd is the detected pressure after combustion; and

Ps is the pressure under a standard known condition.

21. A variable volume ballast chamber for the collection of byproducts of combustion comprising:
a container having an interior wall and a movable piston positioned in said container in sealed engagement with said interior wall;
said container including a sample gas inlet on one side of said piston and said inlet is coupled to an inlet valve;
a sensor coupled to said piston for detecting the position of the piston;
said container including a sample gas outlet on said one side of said piston, said sample gas outlet coupled to an outlet control valve; and
said container including an inlet positioned on the opposite side of said piston for receiving a pressurized fluid for moving said piston to expel collected gases through said sample gas outlet upon application of pressure to said opposite side of said piston.

22. The variable volume ballast chamber as defined in claim 21 wherein said container is cylindrical and includes sealed plates at opposite ends and wherein said sample gas inlet and said sample gas outlet are each formed in one of said sealed plates.

23. The variable volume ballast chamber as defined in claim 22 wherein said sensor is a rotary encoder coupled to said piston by a cable.

24. The variable volume ballast chamber as defined in claim 23 wherein said rotary encoder is mounted to the other of said sealed plates.

25. The variable volume ballast chamber as defined in claim 24 wherein said rotary encoder is mounted to a side of said other of said sealed plates opposite said piston and wherein said other of said sealed plates includes an aperture for coupling said cable to said rotary encoder, and further including a sealing cap sealably positioned over said rotary encoder and wherein said inlet for said pressurized fluid extends through said sealing cap.

26. An elemental analyzer for the determination of the concentration of at least carbon and nitrogen comprising:
a combustion furnace for receiving organic samples for combustion;
a combustion detector coupled to said furnace for receiving byproducts of combustion from said combustion furnace for determining when combustion is completed;
a variable volume ballast chamber coupled to said combustion furnace for receiving byproducts of combustion, said variable volume ballast chamber including a movable piston; and
a control coupled to said combustion detector for the detection of the completion of combustion and sealing byproducts of combustion in said variable volume ballast chamber when combustion is completed;
a sensor for detecting the position of said piston and wherein said control includes a CPU for calculating a volume correction factor for the concentration of gases of the byproducts of combustion based upon the position of said piston.

27. The analyzer as defined in claim 26 wherein said variable volume ballast chamber includes a sample gas inlet and a sample gas outlet on one side of said piston and said control includes valves coupled to said inlet and to said outlet for selectively capturing byproducts of combustion in said variable volume ballast chamber.

28. The analyzer as defined in claim 26 wherein said combustion detector detects $CO_2$.

29. The analyzer as defined in claim 26 wherein said combustion detector detects $H_2O$.

30. The analyzer as defined in claim 26 wherein said variable volume ballast chamber comprises a cylindrical container having a sample gas inlet and a sample gas outlet on one side of said piston and an inlet valve coupled to said inlet and an outlet valve coupled to said outlet.

31. The analyzer as defined in claim 30 wherein said cylindrical container includes a fluid inlet on an opposite side of said piston and a fluid control valve coupled to a source of pressurized fluid to selectively move said piston to force sample gas from said variable volume ballast chamber through said sample gas outlet.

32. The analyzer as defined in claim 31 wherein each of said valves are coupled to said CPU for sequentially actuating said valves to introduce sample gas into said variable volume ballast chamber, allow said sample gas to equilibrate in said variable volume ballast chamber, and subsequently discharge sample gas from said variable volume ballast chamber.

33. The analyzer as defined in claim 32 wherein a $H_2O$ sensor is coupled to said gas outlet of said variable volume ballast chamber to detect the concentration of $H_2$ during an analysis.

34. The analyzer as defined in claim 32 wherein a $CO_2$ sensor is coupled to said gas outlet of said variable volume ballast chamber to detect the concentration of C during an analysis.

* * * * *